(12) United States Patent
Sheehan

(10) Patent No.: US 12,331,008 B2
(45) Date of Patent: *Jun. 17, 2025

(54) SYSTEMS AND METHODS FOR ON-SITE LIQUID ALCOHOL PRODUCTION FROM CARBON DIOXIDE

(71) Applicant: Air Company Holdings, Inc., Brooklyn, NY (US)

(72) Inventor: Stafford W. Sheehan, Tiverton, RI (US)

(73) Assignee: Air Company Holdings, Inc., Brooklyn, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/432,515

(22) Filed: Feb. 5, 2024

(65) Prior Publication Data

US 2024/0174584 A1 May 30, 2024

Related U.S. Application Data

(62) Division of application No. 17/815,332, filed on Jul. 27, 2022, now Pat. No. 11,919,841, which is a (Continued)

(51) Int. Cl.
*C07C 29/158* (2006.01)
*B82Y 30/00* (2011.01)
(Continued)

(52) U.S. Cl.
CPC .......... *C07C 29/158* (2013.01); *C07C 29/151* (2013.01); *C25B 1/04* (2013.01);
(Continued)

(58) Field of Classification Search
CPC ..... C07C 29/151; C07C 29/158; C07C 31/08; C25B 1/04
See application file for complete search history.

(56) References Cited

U.S. PATENT DOCUMENTS

| 8,413,420 | B1 | 4/2013 | Zaromb |
| 11,434,186 | B2 | 9/2022 | Sheehan |

(Continued)

FOREIGN PATENT DOCUMENTS

| CN | 1157281 A | 8/1997 |
| CN | 101830776 A | 9/2010 |

(Continued)

OTHER PUBLICATIONS

Anton et al., Structure-activity relationships of Co-modified Cu/ZnO/Al2O3 catalysts applied in the synthesis of higher alcohols from synthesis gas, Applied Catalysis A: General vol. 505, Sep. 25, 2015, pp. 326-333.*

(Continued)

*Primary Examiner* — Jafar F Parsa
(74) *Attorney, Agent, or Firm* — Foley Hoag LLP; Lucas P. Watkins; Benjamin A. Vaughan

(57) ABSTRACT

Methods for producing alcohols by deriving carbon dioxide from air or another dilute source, and supplying water, which is converted to hydrogen and oxygen, with subsequent conversion of the carbon dioxide and hydrogen into alcohols is disclosed. The method includes, but is not limited to including, a direct air capture system carbon dioxide, a water electrolysis unit powered by electricity, a hydrogenation reactor to convert carbon dioxide and hydrogen gases into alcohols, and a distillation system to separate alcohols or a single constituent alcohol from other hydrogenation products. Optionally, these methods may include systems capture water from air, if water or hydrogen is not available on-site, and the distillation system may use propylene glycol as an extraction solvent. This process can be used for on-site production of feedstock alcohols such as ethanol at high purity, and many other applications.

20 Claims, 3 Drawing Sheets

Related U.S. Application Data division of application No. 16/627,925, filed as application No. PCT/US2018/040442 on Jun. 29, 2018, now Pat. No. 11,434,186.

(60) Provisional application No. 62/630,919, filed on Feb. 15, 2018, provisional application No. 62/528,044, filed on Jul. 1, 2017.

(51) Int. Cl.
  *B82Y 40/00* (2011.01)
  *C07C 29/151* (2006.01)
  *C07C 31/08* (2006.01)
  *C25B 1/04* (2021.01)

(52) U.S. Cl.
  CPC ............... *B82Y 30/00* (2013.01); *B82Y 40/00* (2013.01); *C07C 31/08* (2013.01)

(56) References Cited

U.S. PATENT DOCUMENTS

| | | | |
|---|---|---|---|
| 11,919,841 | B2 | 3/2024 | Sheehan |
| 2004/0259962 | A1 | 12/2004 | Matsui |
| 2007/0282021 | A1 | 12/2007 | Campbell |
| 2010/0280135 | A1 | 11/2010 | Doty |
| 2011/0281961 | A1 | 11/2011 | Bolton et al. |
| 2013/0281553 | A1 | 10/2013 | Kubic et al. |
| 2014/0243435 | A1 | 8/2014 | Blank et al. |
| 2014/0316016 | A1 | 10/2014 | Jennings |
| 2014/0323600 | A1 | 10/2014 | Jennings |
| 2015/0133700 | A1 | 5/2015 | Wollrab et al. |
| 2021/0147326 | A1 | 5/2021 | Sheehan |
| 2023/0060945 | A1 | 3/2023 | Sheehan |

FOREIGN PATENT DOCUMENTS

| | | |
|---|---|---|
| EP | 1452515 A1 | 9/2004 |
| WO | WO-2013/076294 A1 | 5/2013 |
| WO | WO-2019/010095 A1 | 1/2019 |

OTHER PUBLICATIONS

Doss et al., "Optimization of Methanol Synthesis from Carbon Dioxide and Hydrogen: Demonstration of a Pilot-Scale Carbon-Neutral Synthetic Fuels Process", Energy Fuels 2009, 23, 4647-4650.

Extended European Search Report for EP Application No. EP 18829146.2 mailed Feb. 23, 2021.

International Search Report for International Application No. PCT/US18/40442 dated Sep. 24, 2018.

Practical Handbook of Noble Metal Production Technology (vol. Two), Editorial Committee of Practical Handbook of Noble Metal Production Technology, p. 1059, Metallurgical Industry Press (2011).

Zander et al., "The Role of the Oxide Component in the Development of Copper Composite Catalysts for Methanol Synthesis," Angewandte Chemie International Edition 52 (2013): 6536-6540.

* cited by examiner

SYSTEMS AND METHODS FOR ON-SITE LIQUID ALCOHOL PRODUCTION FROM CARBON DIOXIDE

CROSS-REFERENCE TO RELATED APPLICATIONS

This application is a Divisional of U.S. patent application Ser. No. 17/815,332, filed Jul. 27, 2022; which is a Divisional of U.S. patent application Ser. No. 16/627,925, filed Dec. 31, 2019; which is a U.S. National Stage of International Patent Application No. PCT/US2018/040442, filed Jun. 29, 2018; which claims the benefit of U.S. Provisional Patent Application No. 62/630,919, filed on Feb. 15, 2018, and U.S. Provisional Patent Application No. 62/528,044, filed on Jul. 1, 2017. The contents of each of these applications is hereby incorporated by reference in its entirety.

FIELD OF THE INVENTION

The present disclosure relates to carbon dioxide capture and utilization. It focuses on methods that use electricity, heat, or a combination thereof to convert carbon dioxide and water into small molecule alcohols, such as ethanol.

BACKGROUND OF THE INVENTION

As carbon dioxide concentrations in the atmosphere increase, it is becoming advantageous from social welfare, human health, and energy security perspectives to develop technologies that remove carbon dioxide from the air. These technologies have the added benefit of producing commodity chemicals on-site, anywhere on the globe, with no cost or hazard risk of transportation. This need is coupled with an increasing global utilization of renewable electricity generation methods, such as solar photovoltaics and wind turbines. Techniques like these use intermittent energy sources, such as the sun, which sets in the evening and rises in the morning, and wind, which blows intermittently. Thus, the supply of electricity from these sources to electrical grids surges at some points, and is low at others. This presents an opportunity for technologies that can intermittently utilize electricity to produce desired products on-site.

Of the available technologies to produce chemicals from carbon dioxide, hydrogenation of carbon dioxide or carbon monoxide using renewably-derived hydrogen gas from a water electrolyzer is capable of being powered completely by renewable (solar, wind, hydroelectric, etc.) electricity. A method such as this converts a carbon-based feedstock (carbon dioxide or carbon monoxide) and water into hydrocarbon chemicals using an external energy source; this is similar to the fundamental photosynthetic processes enabling life on our planet. For example, plants use photosynthesis to convert carbon dioxide, water, and solar energy into chemical energy by creating sugars and other complex hydrocarbons. This effectively stores the energy from the sun in the chemical bonds of a carbon-based compound. This process has been supporting the Earth's ecosystem and balancing carbon dioxide concentration in our atmosphere for billions of years.

In the last century, human beings have harnessed byproducts of photosynthesis, such as fossil fuels, to provide the energy required for modern life. This has released millions of tons of carbon dioxide into the Earth's atmosphere that had been previously sequestered into the fossil fuels by photosynthesis over the course of millions of years. Scientific evidence points to this rapid increase in carbon dioxide concentration in the atmosphere from anthropogenic sources to be potentially catastrophic to global climate. The development of carbon-negative processes that mimic natural ones to sequester carbon dioxide are, therefore, critical to the future of the planet.

One of the major hurdles toward carbon dioxide sequestration is the effective utilization and catalytic transformation of carbon dioxide and/or carbon monoxide into useful chemicals. Plants achieve this via dehydrogenase enzymes, which utilize transition metals to catalyze the hydrogenation of carbon dioxide into carbon monoxide, formic acid, or a number of other building blocks for sugars. Man-made systems have attempted to copy this route, and chemical methods for carbon dioxide transformation have been known for decades. Many of these, however, have energy requirements unrealistic for any large-scale deployment.

Accordingly, additional systems and methods are needed for sequestering carbon dioxide into useful materials.

SUMMARY OF THE INVENTION

The present disclosure provides systems and methods for the conversion of carbon dioxide to alcohols. Three routes are available, in principle, to perform this reduction reaction: (1) electrolytic carbon dioxide reduction for one-step production of chemicals directly from carbon dioxide, (2) combined electrolysis of water to form hydrogen and oxygen gas, with subsequent hydrogenation of carbon dioxide using hydrogen gas from the electrolyzer in a high pressure, high temperature reactor in a two-step process, and (3) electrolytic carbon dioxide reduction to its most kinetically accessible product, carbon monoxide, and electrolysis of water to form hydrogen and oxygen gas, with subsequent hydrogenation of carbon monoxide using hydrogen gas from the electrolyzer in a high pressure, high temperature reactor (the Fischer-Tropsch process) in a three-step process. The first of these is not practical to carry out based on current technology. The present disclosure provides methods and systems suitable to carry out the second two routes.

The systems and methods of the present disclosure preferably rely on energy derived fom renewable sources to power the conversion of carbon dioxide into alcohol. However, any suitable energy source may be used.

In certain aspects, the systems and methods of the present disclosure operate by separating carbon dioxide from any dilute source (such as air, or a byproduct stream derived from a chemical process), followed by splitting water into hydrogen gas and oxygen gas, then reacting the hydrogen with the carbon dioxide in a hydrogenation reaction to produce alcohols. In certain embodiments, the electrolyzer that produces hydrogen is co-located with the hydrogenation reactor in the same physical area. In other embodiments, the electrolyzer fills a tank with hydrogen, which is then transported to the site of the hydrogenator.

In certain aspects, the systems and methods of the present disclosure operate by separating carbon dioxide from any dilute source (such as air, or a byproduct stream derived from a chemical process), converting the carbon dioxide to carbon monoxide by either thermochemical methods (using hydrogen) or electrochemical methods (using water), then further reacting the carbon dioxide or carbon monoxide with hydrogen, for instance in a Fischer-Tropsch reactor.

In certain embodiments, the alcohols produced according to the present disclosure may be purified by distillation, condensation, or any other suitable method.

In certain aspects, the present disclosure provides integrated systems and methods of using those systems for the production of alcohols from carbon dioxide. In certain embodiments, the systems and methods provided herein react hydrogen with carbon dioxide in a one- or two-step process to produce alcohols. The carbon dioxide may be generated on site or off site. For example, in some embodiments, the carbon dioxide is collected from a source such as air or an industrial waste stream. In other embodiments, the carbon dioxide is provided in substantially pure form. The hydrogen may be generated on site or off site, for instance by an electrolyzer, or may be provided in substantially pure form.

In certain embodiments, the reaction of carbon dioxide with hydrogen to produce alcohols occurs in a one-step process, i.e., one reactor is used to conduct the multiple chemical reactions required to produce alcohols from carbon dioxide. According to such embodiments, the systems of the present disclosure comprise: (1) optionally, an air capture system for collection of carbon dioxide from air, (2) a system that produces hydrogen from water using an electrolyzer, (3) a hydrogenation system that (a) combines the hydrogen produced from the electrolyzer with carbon dioxide from the air capture system to produce carbon monoxide and (b) combines hydrogen produced from the electrolyzer with the carbon monoxide to produce a mixture of alcohols. In further embodiments, the system comprises (5) a distillation unit to purify the alcohol.

In certain embodiments, the reaction of carbon dioxide with hydrogen to produce alcohols occurs in a two-step process, i.e., one reactor is used to conduct the initial reduction of carbon dioxide to carbon monoxide; and a separate reactor is used to conduct the further reduction steps necessary to convert carbon monoxide to alcohols. According to such embodiments, the systems of the present disclosure comprise: (1) optionally, an air capture system for collection of carbon dioxide from air, (2) a system that produces hydrogen from water using an electrolyzer, (3) a first hydrogenation system that combines the hydrogen produced from the electrolyzer with carbon dioxide from the air capture system to produce carbon monoxide, (4) a second hydrogenation system that combines hydrogen produced from the electrolyzer with the carbon monoxide to produce a mixture of alcohols. In further embodiments, the system comprises (5) a distillation unit to purify the alcohol.

In certain embodiments, the methods of the present disclosure comprise capturing carbon dioxide from a dilute source, such as air; electrolyzing water to produce hydrogen; reacting the hydrogen with the carbon dioxide to produce carbon monoxide; and reacting the carbon monoxide with hydrogen to produce an alcohol. In further embodiments, the method further comprises purifying the alcohol, for example by distilling it.

In certain embodiments of the disclosed methods, the two hydrogenation steps are conducted in the same hydrogenation reactor, such that carbon dioxide is reacted with hydrogen gas to directly produce the alcohol. In other embodiments, the two hydrogenation steps are conducted in separate hydrogenation reactors, such that the intermediate product, carbon monoxide, is produced in the first hydrogenation step and used as a reactant in the second hydrogenation step.

Any suitable system for producing hydrogen from water may be used. In certain embodiments, the system that produces hydrogen using electrolysis for later use (such as in the systems and methods disclosed herein) is a polymer electrolyte membrane (PEM) electrolyzer, an alkaline electrolyzer, or a high-temperature solid oxide electrolyzer. Electricity used to drive this process may be obtained from any suitable source, preferably from a renewable resources that do not generate additional carbon dioxide, allowing for a truly carbon-negative solution to our increasing carbon dioxide emissions.

Any suitable system for providing carbon dioxide may be used. In some embodiments of the present disclosure, carbon dioxide is supplied from an air capture system that uses a sorbent to output carbon dioxide at concentrations above 25%, 50%, 75%, 95%, or 99% in air. In other embodiments, carbon dioxide is purchased in its pure form and is source-agnostic. In the case of carbon dioxide that is sourced at concentrations lower than 99%-100%, the hydrogenation system may be modified with catalysts that are capable of selectively hydrogenating carbon dioxide in air, selectively hydrogenating carbon dioxide in air, or selectively hydrogenating carbon dioxide or carbon monoxide in any number of air-derived product streams that contain carbon dioxide, carbon monoxide, or a combination thereof, at any concentration.

In certain embodiments of the present disclosure, carbon dioxide is hydrogenated with hydrogen gas into alcohols. In others, carbon dioxide is hydrogenated to carbon monoxide and water in a first step; then, in a second step the resulting carbon monoxide is hydrogenated into alcohols. In other embodiments, carbon dioxide is electrochemically converted to carbon monoxide and hydrogenated to alcohols in a Fischer-Tropsch-type reactor, which then becomes a component of the overall system.

In certain embodiments of the present disclosure, the resulting product mixture from hydrogenating a carbon dioxide or carbon monoxide feedstock is purified. This can be done either on-site in an integrated system, or off-site in a separate system. This system may be a fractional distiller; it may or may not include molecular sieves and output dehydrated ethanol. This system may be a continuous distillation process. This system may or may not include an extraction solvent.

In certain embodiments, an extraction solvent is used in the distillation process. In further such embodiments, the extraction solvent is propylene glycol. Propylene glycol is a low-cost and non-hazardous extraction solvent. This allows for extractive distillation without the typical extraction solvents that are used for fuel ethanol (for example, benzene). Propylene glycol is a common food additive and is friendly to human health, and can be used in either a fractional distillation batch process or a continuous flow process. The alcohols that are produced from the system may be used for a variety of applications, including for the production of alcoholic spirits, perfume, and other alcohol-based consumer products.

DETAILED DESCRIPTION OF THE INVENTION

Figure 1:
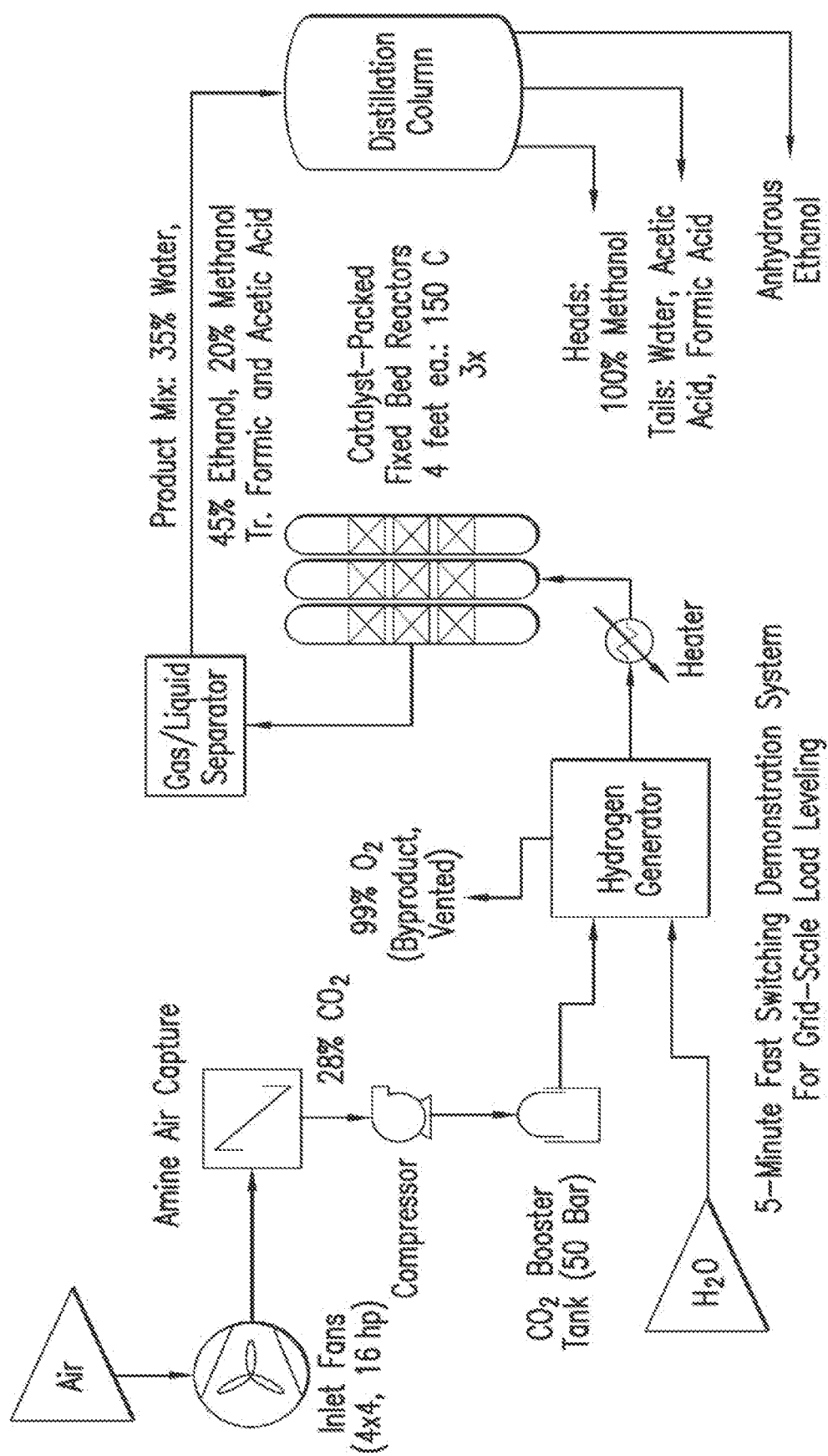
FIG. 1 shows a process flow diagram of an exemplary embodiment, which can be used to produce ethanol using excess electricity from an electrical grid for load-leveling purposes, using an electrolyzer to supply hydrogen gas in a renewable manner and capturing carbon dioxide from the air.

In certain aspects, the present disclosure provides systems for production of alcohols, comprising an electrolyzer; and a hydrogenation reactor configured to convert carbon monoxide to an alcohol, such as ethanol.

In certain embodiments, the hydrogenation reactor is configured to convert carbon dioxide to carbon monoxide and to convert carbon monoxide to an alcohol, such as ethanol. In certain embodiments, the system of any one of the preceding claims, wherein the hydrogenation reactor is configured to react carbon monoxide with hydrogen gas to produce an alcohol, such as ethanol. In further embodiments, the system of any one of the preceding claims, wherein the hydrogenation reactor is configured to react carbon dioxide with hydrogen gas to produce an alcohol, such as ethanol. That is, the hydrogenation reactor is capable of reacting carbon dioxide with hydrogen gas to produce carbon monoxide as an intermediate product, and also capable of further reacting the intermediate carbon monoxide with hydrogen gas to produce the product alcohol.

In certain embodiments, the hydrogenation reactor operates with selectivity for the alcohol of greater than 10%. In certain embodiments, the selectivity for the alcohol is greater than 30%. The selectivity may be provided by suitable selection of catalyst. In certain embodiments, the hydrogenation reactor comprises a first catalyst comprising platinum, palladium, copper, cobalt, zinc, selenium, rhodium, iron, molybdenum, sulfur, oxygen, or alloys or chemical compounds thereof. In certain embodiments, the first catalyst comprises nanoparticles comprising CuZn, CuZnFeK, CuZnFcKC, CuZnFcAlK, CuZnFcNa, CuZnFcCoK, CuZnFcCoNaK, CuCoAl, CoMOSK, CuZnK, CuCoMn, RhRu, PdCuFe, Rh, or RhFeSi, optionally on an alumina support. In certain embodiments, the first catalyst comprises nanoparticles comprising CoMoSK, optionally on an alumina support. In certain embodiments, the first catalyst comprises nanoparticles comprising rhodium, optionally on a high surface area support.

In certain embodiments, the system further comprises a reduction reactor configured to convert carbon dioxide to carbon monoxide. The reduction reactor may produce substantially pure carbon monoxide (e.g., carbon monoxide gas comprising less than 30%, 20%, 10%, or 5% carbon dioxide gas an an impurity), or may simply enrich the carbon dioxide stream in carbon monoxide prior to further reaction in the hydrogenation reactor. In certain embodiments, the reduction reactor is an electrochemical reactor. In other embodiments, the reduction reactor is a carbon dioxide hydrogenation reactor.

In certain embodiments, the reduction reactor is configured to react carbon dioxide with hydrogen gas, thereby producing carbon monoxide. In certain embodiments, the reduction reactor operates with selectivity for carbon monoxide greater than 10%. In certain embodiments, the reduction reactor operates with selectivity for carbon monoxide greater than 50%. The selectivity may be provided by suitable selection of catalyst. In certain embodiments, the reduction reactor comprises a second catalyst comprising platinum, palladium, copper, cobalt, zinc, selenium, rhodium, iron, oxygen, or alloys or chemical compounds thereof. In certain embodiments, the second catalyst comprises nanoparticles comprising CuZn, CuZnFeK, CuZnFcKC, CuZnFcAlK, CuZnFeNa, CuZnFeCoK, CuZnFeCoNaK, CuCoAl, CoMoSK, CuZnK, CuCoMn, RhRu, PdCuFe, Rh, or RhFeSi, optionally on an alumina support.

In certain embodiments, the system comprises a direct air capture system. In certain embodiments, the direct air capture system is configured for carbon dioxide purification from ambient air.

In certain embodiments, the system comprises a distillation system. In certain embodiments, the distillation system is configured to separate the liquid alcohol, such as ethanol, from other products made in the hydrogenation reactor. In certain embodiments, the distillation system comprises propylene glycol.

In certain preferred embodiments, the alcohol is ethanol.

In certain embodiments, the system comprises one or more solar photovoltaic panels.

In certain embodiments, the electrolyzer is configured to split water into hydrogen and oxygen gas.

In certain aspects, the present disclosure provides methods for producing an alcohol, comprising electrolyzing water to produce hydrogen; converting carbon monoxide to an alcohol, such as ethanol; and optionally, distilling the alcohol.

In certain embodiments, the method further comprises converting carbon dioxide to carbon monoxide.

In certain embodiments, the steps of converting carbon dioxide to carbon monoxide and converting carbon monoxide to the alcohol occur in a single hydrogenation reactor. That is, the single hydrogenation reactor is configured to perform both steps sequentially.

In certain embodiments, converting carbon monoxide to the alcohol comprises reacting carbon monoxide with hydrogen in the presence of a first catalyst comprising platinum, palladium, copper, cobalt, zinc, selenium, rhodium, iron, molybdenum, sulfur, oxygen, or alloys or chemical compounds thereof. In certain embodiments, reacting carbon monoxide with hydrogen comprises reacting carbon monoxide with hydrogen in the presence of a first catalyst comprising nanoparticles comprising CuZn, CuZnFeK, CuZnFeKC, CuZnFeAlK, CuZnFeNa, CuZnFcCoK, CuZnFeCoNaK, CuCoAl, CoMOSK, CuZnK, CuCoMn, RhRu, PdCuFe, Rh, or RhFeSi, optionally on an alumina support. In certain embodiments, reacting carbon monoxide with hydrogen comprises reacting carbon monoxide with hydrogen in the presence of a first catalyst comprising nanoparticles comprising CoMoSK, optionally on an alumina support. In certain embodiments, reacting carbon monoxide with hydrogen comprises reacting carbon monoxide with hydrogen in the presence of a first catalyst comprising nanoparticles comprising rhodium, optionally on a high surface area support.

In certain embodiments, converting carbon dioxide to carbon monoxide takes place in a different reactor from the reactor in which converting carbon monoxide to an alcohol takes place.

In certain such embodiments, converting carbon dioxide to carbon monoxide comprises electrochemically reducing carbon dioxide to produce carbon monoxide. In other such embodiments, converting carbon dioxide to carbon monoxide comprises reacting carbon dioxide with hydrogen from the electrolyzing step to produce carbon monoxide. In certain embodimentsm, converting carbon dioxide to carbon monoxide comprises reacting carbon dioxide with hydrogen in the presence of a second catalyst comprising nanoparticles comprising platinum, palladium, copper, cobalt, zinc, selenium, rhodium, iron, oxygen, or alloys or chemical compounds thereof. In certain embodiments, converting carbon dioxide to carbon monoxide comprises reacting carbon dioxide with hydrogen in the presence of a second catalyst comprising nanoparticles comprising CuZn, CuZn-FeK, CuZnFeKC, CuZnFeAlK, CuZnFeNa, CuZnFeCoK, CuZnFeCoNaK, CuCoAl, CoMOSK, CuZnK, CuCoMn, RhRu, PdCuFe, Rh, or RhFeSi, optionally on an alumina support.

In certain embodiments, the method further comprises capturing carbon dioxide from an input stream. In certain such embodimets, the input stream is air. In other such embodiments, the input stream is an industrial waste or byproduct stream.

In certain embodiments, wherein the distilling step comprises distilling the alcohol in the presence of propylene glycol.

DISCUSSION

In the most general form of the systems and methods disclosed herein, the overall reaction that occurs is the reduction of carbon dioxide and oxidation of water to form oxygen, preferably using renewable energy to power the process. This is shown in the reaction scheme below:

$$xCO_2 + yH_2O \rightarrow Products + zO_2$$

Where x, y, z are stoichiometric coefficients and are dependent on the product being made by the carbon dioxide reduction reaction. Common products of this reaction include, but are not limited to, CO, $HCO_2H$, HCHO, $CH_3OH$, $CH_4$, $CH_3CH_2OH$, $CH_3CH_3$. For the purposes of the present disclosure, the desired products are alcohols, preferably ethanol ($CH_3CH_2OH$), thus the following overall reaction (or a similar version of it) is desired:

$$2CO_2 + 6H_2O \rightarrow 2CO_2 + 6H_2 + 3O_2 \rightarrow CH_3CH_2OH + 3H_2O + 3O_2$$

In some embodiments of the disclosure, other products are produced as impurities, but may be separated in a final distillation or condensation step of the current system. Common products of this reaction noted above are typical impurities that are removed. In many cases, the overall concentration of ethanol pre-distillation is much less than the concentration of the other products. The ethanol concentration in the output aqueous alcohol mixture from the hydrogenation reactor can be as low as 99%, 95%, 90%, 50%, 30%, 20%, 10%, 5%, or 1% ethanol or lower.

Figure 2:
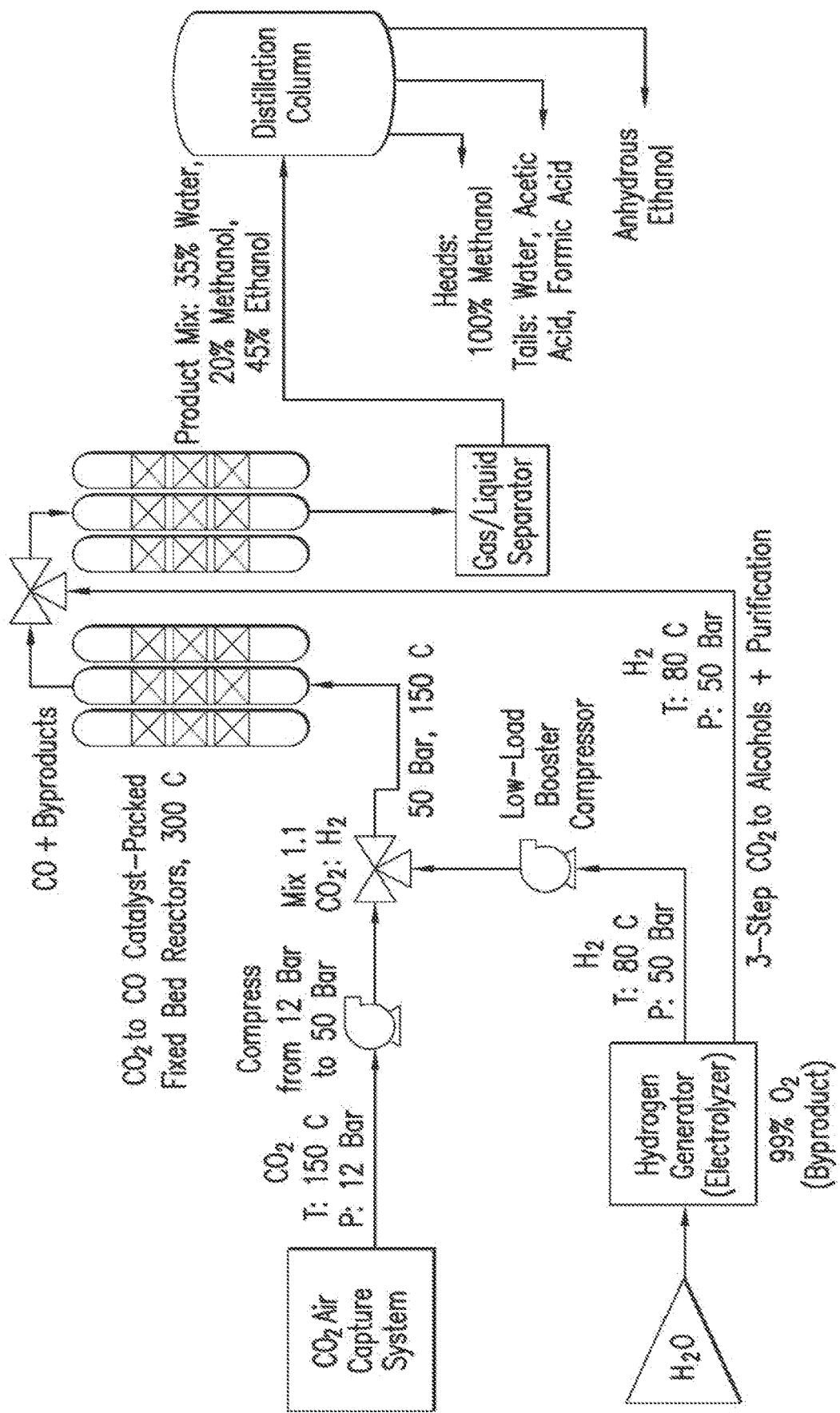
FIG. 2 shows a process flow diagram of an exemplary embodiment, where ethanol is produced from carbon dioxide in a three-step process utilizing thermochemical conversion of carbon dioxide and hydrogen to carbon monoxide, then sequential conversion of carbon monoxide and hydrogen to alcohols.
Figure 3:
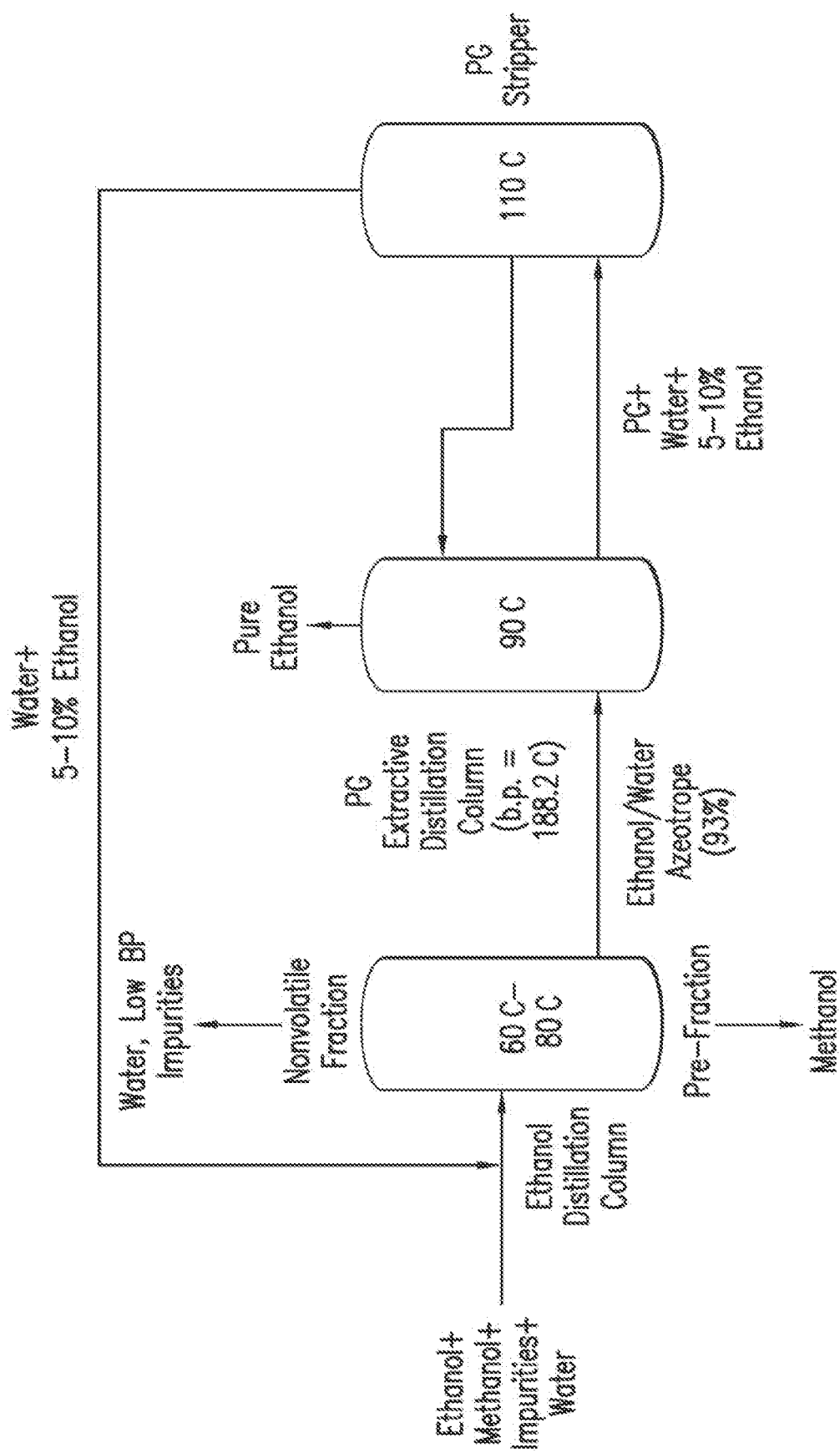
FIG. 3 shows a process flow diagram of another apparatus of the present disclosure, wherein propylene glycol is used as an extraction solvent for extractive distillation of non-hazardous ethanol.

The above reaction is accomplished using atmospheric carbon dioxide, water, and an energy source, preferably a renewable energy source (including, but not limited to, solar or wind energy) using the system that is an object of the present disclosure. This is done by arranging the different components, (1)-(5) in unique configurations. This disclosure includes, but is not limited to, configurations of steps (1)-(5) wherein carbon dioxide capture happens concurrent to water capture or water is also captured from the air, water splitting powered by a solar photovoltaic array is then performed to produce hydrogen gas from the water, followed by hydrogenation to form ethanol and impurities, followed by removal of the impurities. The sequence of the steps is outlined in FIGS. 1-3 above, and must include conversion of water into hydrogen gas prior to hydrogenation, and may include condensation/distillation (removal of impurities) after hydrogenation.

In some embodiments of the disclosure, different technologies can suffice for the individual components (1)-(5) of the liquid alcohol production system. Additional components, including valves, compressors, pumps, mixers, and other suitable systems known to those skilled in the art are also utilized. These components are outlined as follows:

(1) Optional system for the collection of carbon dioxide: This process includes, but is not limited to, a carbon dioxide scrubber. Carbon dioxide scrubbers, such as is the object of the component of the disclosure, typically operate by binding carbon dioxide to either a solid or a liquid sorbent, such as an amine, such as monoethanolamine, and reversing the binding at higher temperatures. In some cases, these amines are embedded in a membrane as a part of porous granulates, a binding event which can be reversed at moderate temperatures (c.a. 100° C.). Another method of collection of carbon dioxide from air is the use of a zeolite or molecular sieve similar to vacuum swing or pressure swing adsorption systems for oxygen or nitrogen putification from air. In some cases, liquid air energy storage systems can be utilized to capture carbon dioxide from the air. Scrubbing processes that utilize sodium hydroxide, lithium hydroxide, calcium oxide, limestone, or other carbonate-based or basic chemical cycles are also useful for this step.

In one example, carbon dioxide is absorbed by an alkaline sodium hydroxide solution in water to produce sodium carbonate in an exothermic adsorption reaction. Causticization to transfer carbonate anions from the sodium cation to a calcium cation can then be utilized, and calcination of calcium carbonate can be used to produce $CO_2$ and calcium oxide. Calcium oxide can then be regenerated with water. Lithium hydroxide systems can achieve this cycle without having to use a calcium cation.

(2) Water splitting electrolyzer: This component may comprise any suitable type of electrolyzer, such as polymer electrolyte membrane (PEM) electrolyzers, alkaline electrolyzers, and solid oxide electrolyzers. In a water splitting electrolyzer, water (sometimes further deionized by an onboard ion exchange column) is fed into an anode chamber where it is oxidized using electricity to oxygen gas. The remaining protons are transferred to a cathode where they are reduced to hydrogen gas. The oxygen gas is removed from the anode and can be either used or vented, and the hydrogen gas that is produced separately from the oxygen at the cathode can be further utilized.

PEM electrolyzers have the advantage of using a polymer electrolyte membrane, typically Nafion, between the anode and cathode. In a PEM electrolyzer, high purity water is fed through an anode flow plate adjacent to a catalyst coated membrane and diffusion layer. At the catalyst-coated membrane, the water is oxidized to oxygen gas, for example using an iridium oxide nanoparticle based anode, which is carried out through the flow plate. Electrons liberated by the process are transferred to the cathode through an external circuit, where a voltage is applied (typically 1.5 V-2.2 V). Protons are transported through the Nafion membrane to a platinum cathode on the opposite side of the catalyst coated membrane. The protons are then reduced to hydrogen gas. PEM electrolyzers have the added benefit of production of high-pressure hydrogen due to electrochemical pressure generated by conversion of a gas to a liquid. In these systems, hydrogen at pressures >100 psi can be generated without the need for a compressor. Alkaline electrolyzers are also useful for this application, wherein a polymer electrolyte membrane is not used.

(3) Carbon dioxide hydrogenation reactor: Hydrogenation reactions such as are described herein use heat and pressure to react hydrogen gas with a low-energy carbon-based reactant, in this case carbon dioxide. This reaction is performed with a heterogeneous catalyst present inside the reactor, wherein the reactant products bind to the surface of the catalyst and are rearranged depending on the surface properties of the catalyst. The use of heat allows for reduction of $CO_2$ to either CO or directly to alcohols, enabling bond formation to overcome activation barriers present on the surface of the catalyst, while pressure improves the rate of reaction. Selectivity of the process is controlled by the catalyst, on which both heat and pressure have an effect. The hydrogenation reactors described in this step have selectivity for CO of 5%, 10%, 25%, 50%, 75%, 80%, 85%, 90%, 95%, 99%, 99.9%, or higher.

In some embodiments of the present disclosure, carbon dioxide is fed into a hydrogenation reactor to reduce it to an intermediate step prior to ethanol production. In some cases, this intermediate step is production of carbon monoxide and water from carbon dioxide and hydrogen as is noted in this step. Temperature and pressure are critical for tuning reaction conditions. In some embodiments of the present disclosure, the pressure vessel is able to withstand pressures up to 10 psi, 100 psi, 500 psi, 1000 psi, 1500 psi, 2000, psi, 3000 psi, 5000 psi, 10,000 psi, and higher. The ratio of pressures between hydrogen gas and carbon dioxide, for example, can also affect selectivity and yield of the process. In some embodiments, the partial pressure of carbon dioxide gas is 50 psi, 100 psi, 200 psi, 400 psi, 600 psi, 800 psi, or higher. The partial pressure of hydrogen is typically higher than that of carbon dioxide, and in some embodiments the partial pressure of hydrogen is 100 psi, 300 psi, 500 psi, 800 psi, 1000 psi, 2000 psi, 5000 psi, or higher. In some embodiments, the carbon dioxide is present in the liquid phase, in which the partial pressure of the liquid is higher than 860 psi at room temperature (25° C.). Pressures can include 1000 psi, 2000 psi, 5000 psi, or higher.

Temperatures that this reaction can be accomplished at using the catalysts described herein range from 100° C., 200° C., 400° C., 500° C., 700° C., and higher. Typical temperature ranges are between 150° C. and 350° C. When the reactant gases are introduced to a chemical reactor at these temperatures and the aforementioned pressures with the catalysts described herein, carbon monoxide and/or alcohols can be produced.

Suitable catalysts for the process include, but are not limited to, alloys of copper and zinc in nanoparticulate form, copper nanoparticles, cobalt nanoparticles, iron nanoparticles, and other nanoparticles or high surface area materials with particle or pore sizes ranging from 0.5 nm-10 nm, that are embedded on a high surface are support such as carbon black, silica, or titanium dioxide. In some cases, the support is comprised of high surface area alumina, in others it is approximately 15-30 nm average particle size of mixed phase titanium dioxide (anatase and rutile). In others, the support is purely one phase of either titania or alumina. In others, the support is comprised of nanoparticles 10 nm, 20 nm, 50 nm, 100 nm, 500 nm, and higher. The support can be made using a variety of oxides, including but not limited to $Al_2O_3$, $ZrO_2$, $SnO_2$, $SiO_2$, $ZnO_2$, $TiO_2$, and others. It can also be comprised of mesoporous silica or a variety of carbon allotropes. Silicates, nitrides, fluorides, and other compounds can also be used as support materials.

Variations in catalyst formulation include ratios of Cu:Zn between 1:0, 10:1, and 100:1, or Mo:Fe between 1:5, 1:3, 1:2, 1:1, 2:1, 3:1, or 5:1, or Co:Cu between 1:5, 1:3, 1:2, 1:1, 2:1, 3:1, or 5:1. For Cu:Zn usable ratios are between 1:1, 2:1, 3:1, 5:1, and higher for Zn, and 1:2, 1:3, 1:5, and higher for Cu. In some cases, additional compounds can be introduced to the particles or can be made into separate catalysts themselves, which can include one or more of the following: Pt, Ru, Rh, Ir, Au, Ni, Co, Li, Na, Fe, Zn, K, Sc, Ca, Mg, Mn, Sr, Ba, Ag, Sm, La, Ti, V, Zr, Nb, Mo, Re, Sn, Ce, or other elements. Substitution of platinum, palladium, copper, cobalt, selenium, rhodium, or iron with other elements in its group or with similar valence configurations are also methods of producing catalysts as described in this disclosure. In certain embodiments, the catalyst comprises nanoparticles comprising CuZnFeK, CuZnFeKC, CuZnFcAIK, CuZnFcNa, CuZnFeCoK, CuZnFeCoNaK, CuCoAl, CoMOSK, CuZnK, CuCoMn, RhRu, PdCuFe, Rh, or RhFeSi.

Synthetic methods for production of these catalytic nanoparticles and mesoporous materials include synthesis from nitrate, chloride, fluoride, halide, acetylacetonate, acetate, amine, carboxylic acid, and other chemical precursors. Synthetic methods can include, but are not limited to, ultrasonication, thermal annealing, sol-gel methods, freezing, wet/dry impregnation, and other methods. In some cases, the catalyst will produce a side-product, including but not limited to methanol, methane, formic acid, paraffins, or other products.

In some cases, the catalyst present in (4) is sufficient to convert hydrogen and carbon dioxide into liquid alcohols, specifically ethanol, at high enough selectivity to suffice for application of the presently disclosed methods. In these cases, a second hydrogenation reactor is not necessary, as both hydrogenation steps occur within the same reactor. That is, the carbon dioxide does not need to be pre-processed into carbon monoxide before generating ethanol.

(4) Ethanol hydrogenation reactor:

Hydrogenation of carbon-based feedstocks with hydrogen gas has the advantage of being tunable by changing the catalyst present in the reactor, which requires minimal changes in overall reactor design. This component of the present disclosure utilizes catalyst formulations, including but not limited to copper, zinc, and iron alloys or mixed oxides on high surface area supports, such as alumina, that produce ethanol with high selectivity. Due to the variety of products that can be produced by hydrogenation processes, selectivity is a critical metric in determining efficacy of a catalyst. The hydrogenation reactors described herein have selectivity for liquid alcohol, and specifically ethanol, production among liquid products of 5%, 10%, 25%, 50%, 75%, 80%, 85%, 90%, 95%, 99%, 99.9%, or higher.

Temperature and pressure are critical for tuning reaction conditions. In some embodiments of the present disclosure, the pressure vessel is able to withstand pressures up to 10 psi, 100 psi, 500 psi, 1000 psi, 1500 psi, 2000, psi, 3000 psi, 5000 psi, 10,000 psi, and higher. The ratio of pressures between hydrogen gas and carbon dioxide, for example, can also effect selectivity and yield of the process. In some embodiments, the partial pressure of carbon dioxide gas is 50 psi, 100 psi, 200 psi, 400 psi, 600 psi, 800 psi, or higher. The partial pressure of hydrogen is typically higher than that of carbon dioxide, and in some embodiments the partial pressure of hydrogen is 100 psi, 300 psi, 500 psi, 800 psi, 1000 psi, 2000 psi, 5000 psi, or higher. In some embodiments, the carbon dioxide is present in the liquid phase, in which the partial pressure of the liquid is higher than 860 psi at room temperature (25° C.). Pressures can include 1000 psi, 2000 psi, 5000 psi, or higher.

Temperatures that this reaction can be accomplished at using the catalysts described herein range from 100° C., 200° C., 400° C., 500° C., 700° C., and higher. Typical temperature ranges are between 150° C. and 350° C. When the reactant gases are introduced to a chemical reactor at these temperatures and the aforementioned pressures with the catalysts described herein, ethanol can be produced.

Catalysts for the process include, but are not limited to, alloys of copper, zinc, and iron in nanoparticulate form, combinations of cobalt metal and molybdenum sulfide in nanoparticulate form, rhodium nanoparticles, rhodium selenide nanoparticles, palladium nanoparticles, platinum nanoparticles, platinum/cobalt nanoparticles, palladium/copper nanoparticles, and other nanoparticles or high surface area materials with particle or pore sizes ranging from 0.5 nm-10 nm, that are embedded on a high surface are support such as carbon black, silica, or titanium dioxide. In some cases, the support is comprised of high surface area alumina, in others it is approximately 15-30 nm average particle size of mixed phase titanium dioxide (anatase and rutile). In others, the support is purely one phase of either titania or alumina. In others, the support is comprised of nanoparticles 10 nm, 20 nm, 50 nm, 100 nm, 500 nm, and higher. The support can be made using a variety of oxides, including but not limited to $Al_2O_3$, $ZrO_2$, $SnO_2$, $SiO_2$, $ZnO_2$, $TiO_2$, and others. It can also be comprised of mesoporous silica or a variety of carbon allotropes. Silicates, nitrides, fluorides, and other compounds can also be used as support materials.

Variations in catalyst formulation include ratios of Cu:Zn:Fe between 1:1:1, 100:1:1, 1:100:1, 1:1:100 and between. These may be present in oxide form, or metal form upon production. Other variants include $Co:MoS_2$ between 1:100, 1:5, 1:3, 1:2, 1:1, 2:1, 3:1, 5:1, or 100:1, Co:MoS:K between 1:1:100, 1:1:5, 1:3:2, 1:2:2, 1:1:1, 2:1:1, 3:1:3, 1:5:1, or 1:100:1. Rh:Se between 1:0, 10:1, and 100:1, or Pt:Cu between 5:1, 3:1, 2:1, 1:1, 2:1, 3:1, or 5:1, or Pt:Co between 5:1, 3:1, 2:1, 1:1, 2:1, 3:1, or 5:1. For Pd:Cu usable ratios are between 1:1, 2:1, 3:1, 5:1, and higher for Pd, and 1:2, 1:3, 1:5, and higher for Cu. In some cases, additional compounds can be introduced to the particles or can be made into separate catalysts themselves, which can include one or more of the following: Pt, Ru, Rh, Ir, Au, Ni, Co, Li, Na, Fe, Zn, K, Se, Ca, Mg, Mn, Sr, Ba, Ag, Sm, La, Ti, V, Zr, Nb, Mo, Re, Sn, Ce, or other elements. Substitution of platinum, palladium, copper, cobalt, selenium, rhodium, or iron with other elements in its group or with similar valence configurations are also methods of producing catalysts as described in this disclosure. In certain embodiments, the catalyst comprises nanoparticles comprising CuZnFeK, CuZnFeKC, CuZnFeAlK, CuZnFeNa, CuZnFeCoK, CuZnFeCoNaK, CuCoAl, CoMOSK, CuZnK, CuCoMn, RhRu, PdCuFe, Rh, or RhFeSi.

Synthetic methods for production of these catalytic nanoparticles and mesoporous materials include synthesis from nitrate, chloride, fluoride, halide, acetylacetonate, acetate, amine, carboxylic acid, and other chemical precursors. Synthetic methods can include, but are not limited to, ultrasonication, thermal annealing, sol-gel methods, freezing, wet/dry impregnation, and other methods.

Reactors for steps (3) and (4) may include, but are not limited to, fixed bed flow reactors, continuous stirred tank reactors, mixed tubular fixed-bed reactors, entrained flow reactors, slurry reactors, trickle-bed reactors, circulating catalyst reactors, fluidized-bed reactors, or others. In some cases, the same type of reactor is used for steps (3) and (4); in others, they are different types of reactors.

In some embodiments of this disclosure, the feed carbon dioxide containing stream is compressed prior to introduction to the hydrogenation reactor. In others, it is liquefied using a thermal process. The present disclosure provides systems that are compatible with high pressure gaseous carbon dioxide, high pressure liquid carbon dioxide, or both. The variable pressure nature of this system allows either gaseous carbon dioxide, liquid carbon dioxide, liquefied air, or any gaseous or liquid phase of a carbon-containing feed stream to be utilized. Furthermore, the present disclosure provides systems in which this carbon-containing stream may be fed at variable pressures into a hydrogenation reactor.

(5) Purification systems: This component includes, but is not limited to, a distillation or condensation apparatus to remove the aforementioned impurities from ethanol produced in the hydrogenation reactor. In some embodiments of the current disclosure, the products from the hydrogenation reactor are vapor phase due to the high temperatures used in the reactor. In this case, a condensation system that is kept at a constant temperature near the boiling point of ethanol (78.4° C.) can be used to separate the ethanol from other impurities. Many other methods, such as fractional separation, centrifugation, and others can be used to separate ethanol vapor from other vaporous products In other embodiments, the products of the hydrogenation reaction are allowed to cool. In this case, distillation will be performed to separate the ethanol from other products of the hydrogenation reaction. Distillation can be accomplished in batch or continuous systems, using fractional distillation, steam distillation, vacuum distillation, short path distillation, zone distillation, or other techniques. Pressure-swing and azeotropic distillation techniques can also be used to purify the ethanol from other impurities. The condensate will ideally be high purity ethanol; however, minor impurities may sometimes be present.

In some embodiments of the present disclosure, an extractive distillation system will be used. This enables removal of water and aqueous impurities from ethanol at low input energy, at higher purity, or at low process times. While benzene and ethylene glycol have been used as extraction solvents for the extractive distillation of pure ethanol, they are not compatible with consumer products, since they are hazardous and toxic even at low concentrations. Propylene glycol, however, is a healthy and non-hazardous compound present as a sweetener in foods and a solvent for electronic cigarettes. In some embodiments of this disclosure, propylene glycol is used as an extractive distillation solvent. This can be accomplished in either a batch or continuous process.

EXAMPLES

The invention now being generally described, it will be more readily understood by reference to the following examples which are included merely for purposes of illustration of certain aspects and embodiments of the present invention, and are not intended to limit the invention.

Example 1: Preparation of Methanol and Ethanol from Carbon Dioxide

A Proton C10 polymer electrolyte membrane electrolyzer was used to fill a hydrogen tank to 2000 psi. Hydrogen was drawn from a tank at 1000 psi using a down-pressure regulator. Concurrently, carbon dioxide was drawn from a tank at high pressure using a Haskel compressor, then vaporized into a supercritical fluid at 1000 psi. Separately, the 1000 psi streams of $H_2$ and $CO_2$ were heated using an electric heater to 300° C. The 300° C. gas streams were then blended in a 2:1 $H_2:CO_2$ ratio using mass flow controllers. The blended 1000 psi gas was fed at a variable gas hourly space velocity between 1000 and 5000 mL per gram of catalyst per hour into a half-inch inner diameter tubular fixed-bed reactor packed with a CuZnFeCoK catalyst supported on alumina. The bottom 8 inches of the reactor was packed with inert alumina with the same particle size and morphology as the alumina that the catalyst is suspended on, to prevent contamination of catalyst into the gaseous output stream. At the surface of the catalyst, the $H_2$ and $CO_2$ gases are reacted to form methanol, ethanol, and methane ($CH_4$), all being in gaseous form with approximately 20% of the $CO_2$ being reacted in the first pass. The gases are then cooled so that the room-temperature liquids (methanol and ethanol) condense out. These liquids are separated from the $H_2$, $CO_2$, and $CH_4$ at a gas-liquid separator. The gases are recycled to be re-used as a feed, while the liquids are distilled and utilized.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

I claim:

1. A method for production of an alcohol, comprising:
   electrolyzing water to produce hydrogen;
   combining carbon dioxide with the hydrogen in the presence of a first catalyst to produce a mixture of alcohols, wherein the mixture of alcohols comprises ethanol; and
   wherein the first catalyst comprises nanoparticles comprising copper and zinc.

2. The method of claim 1, wherein the first catalyst comprises CuZn, CuZnFeK, CuZnFeKC, CuZnFeAlK, CuZnFeNa, CuZnFeCoK, CuZnFeCoNaK, or CuZnK, optionally on an alumina support.

3. The method of claim 2, wherein the first catalyst comprises CuZn, optionally on an alumina support.

4. The method of claim 2, wherein the first catalyst comprises CuZnFeK, optionally on an alumina support.

5. The method of claim 2, wherein the first catalyst comprises CuZnFeKC, optionally on an alumina support.

6. The method of claim 2, wherein the first catalyst comprises CuZnFeAlK, optionally on an alumina support.

7. The method of claim 2, wherein the first catalyst comprises CuZnFeNa, optionally on an alumina support.

8. The method of claim 2, wherein the first catalyst comprises CuZnFeCoK, optionally on an alumina support.

9. The method of claim 2, wherein the first catalyst comprises CuZnFeCoNaK, optionally on an alumina support.

10. The method of claim 2, wherein the first catalyst comprises CuZnK, optionally on an alumina support.

11. The method of claim 1, wherein the first catalyst further comprises cobalt, selenium, sodium, potassium, iron, molybdenum, sulfur, oxygen, or alloys or chemical compounds thereof.

12. The method of claim 11, wherein the first catalyst comprises sodium.

13. The method of claim 11, wherein the first catalyst comprises CuZnFeK, CuZnFeKC, CuZnFeAlK, CuZnFeNa, CuZnFeCoK, CuZnFeCoNaK, or CuZnK, optionally on an alumina support.

14. The method of claim 1, further comprising capturing carbon dioxide from an input stream prior to combining the carbon dioxide with the hydrogen.

15. The method of claim 14, wherein the input stream is air, an industrial waste stream, or a byproduct stream.

16. The method of claim 14, wherein the first catalyst further comprises cobalt, selenium, sodium, potassium, iron, molybdenum, sulfur, oxygen, or alloys or chemical compounds thereof.

17. The method of claim 16, wherein the first catalyst comprises CuZnFeK, CuZnFeKC, CuZnFeAlK, CuZnFeNa, CuZnFeCoK, CuZnFeCoNaK, or CuZnK, optionally on an alumina support.

18. The method of claim 1, further comprising distilling the mixture of alcohols.

19. The method of claim 18, wherein the first catalyst further comprises cobalt, selenium, sodium, potassium, iron, molybdenum, sulfur, oxygen, or alloys or chemical compounds thereof.

20. The method of claim 1, wherein the mixture of alcohols further comprises methanol.

* * * * *